(12) United States Patent
Chapa et al.

(10) Patent No.: US 9,050,465 B2
(45) Date of Patent: Jun. 9, 2015

(54) METHODS AND SYSTEMS FOR FACILITATING ADJUSTMENT OF ONE OR MORE FITTING PARAMETERS BY AN AUDITORY PROSTHESIS PATIENT

(75) Inventors: Fernando Chapa, Quartz Hill, CA (US); Guillermo A. Calle, Moorpark, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/122,244

(22) PCT Filed: May 22, 2012

(86) PCT No.: PCT/US2012/038984
§ 371 (c)(1),
(2), (4) Date: Nov. 25, 2013

(87) PCT Pub. No.: WO2012/162312
PCT Pub. Date: Nov. 29, 2012

(65) Prior Publication Data
US 2014/0114375 A1    Apr. 24, 2014

Related U.S. Application Data

(60) Provisional application No. 61/490,566, filed on May 26, 2011.

(51) Int. Cl.
*A61N 1/00* (2006.01)
*A61N 1/36* (2006.01)
*H04R 25/00* (2006.01)

(52) U.S. Cl.
CPC ............ *A61N 1/36032* (2013.01); *H04R 25/00* (2013.01); *H04R 2225/61* (2013.01); *H04R 25/50* (2013.01)

(58) Field of Classification Search
CPC .................................................. A61N 1/36032
USPC ............................................. 607/57; 381/314
See application file for complete search history.

(56) References Cited

U.S. PATENT DOCUMENTS

| 7,043,303 | B1* | 5/2006 | Overstreet | 607/57 |
| 7,672,468 | B2* | 3/2010 | Kaiser et al. | 381/314 |
| 2005/0249368 | A1 | 11/2005 | Menzl et al. | |
| 2007/0076909 | A1 | 4/2007 | Roeck et al. | |
| 2009/0052705 | A1 | 2/2009 | Binder et al. | |
| 2009/0074215 | A1* | 3/2009 | Schumaier | 381/314 |

FOREIGN PATENT DOCUMENTS

EP    1653775    5/2006

OTHER PUBLICATIONS

International Search Report and Written Opinion received in International Application No. PCT/US12/038984 dated Aug. 9, 2012.
Communication pursuant to Article 94(3) EPC received in European Patent Application No. 12725970.3, dated Oct. 9, 2014.

* cited by examiner

*Primary Examiner* — Amanda Patton
*Assistant Examiner* — Nadia A Mahmood
(74) *Attorney, Agent, or Firm* — ALG Intellectual Property, LLC

(57) ABSTRACT

An exemplary method of facilitating adjustment of one or more fitting parameters by an auditory prosthesis patient includes 1) receiving, by a fitting subsystem communicatively coupled to a sound processor, user input representative of a selection of a fitting parameter, 2) associating, by the fitting subsystem in response to the user input, the fitting parameter with a physical input mechanism that is a part of the sound processor, and 3) dynamically adjusting, by the fitting subsystem, a value of the fitting parameter in response to actuation by a user of the physical input mechanism. Corresponding methods and systems are also described.

19 Claims, 11 Drawing Sheets

US 9,050,465 B2

METHODS AND SYSTEMS FOR FACILITATING ADJUSTMENT OF ONE OR MORE FITTING PARAMETERS BY AN AUDITORY PROSTHESIS PATIENT

RELATED APPLICATIONS

The present application claims priority to U.S. Provisional Patent Application No. 61/490,566 by Fernando Chapa et al., filed on May 26, 2011, and entitled "METHODS AND SYSTEMS FOR FACILITATING ADJUSTMENT OF ONE OR MORE FITTING PARAMETERS BY AN AUDITORY PROSTHESIS PATIENT," the contents of which are hereby incorporated by reference in their entirety.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to stimulation sites (e.g., auditory nerve fibers) by way of one or more channels formed by an array of electrodes implanted in an auditory prosthesis patient. Direct stimulation of the stimulation sites leads to the perception of sound in the brain and at least partial restoration of hearing function.

When an auditory prosthesis (e.g., a cochlear implant) is initially implanted in a patient, and during follow-up tests and checkups thereafter, it is usually necessary to fit the auditory prosthesis system to the patient. Fitting of an auditory prosthesis system to a patient is not an exact science but an ongoing trial-and-error-based iterative exercise that is largely dependent on the experience of and feedback provided by the patient. For example, in a fitting session, an audiologist or the like typically adjusts the value of a particular fitting parameter and relies on subjective feedback from the patient as to the effect of the adjustment. This iterative process may continue for some time until the audiologist converges on an optimal value for the fitting parameter. Unfortunately, the audiologist typically has to adjust a multitude of fitting parameters in this manner, thus causing the fitting session to be both labor and time intensive.

SUMMARY

An exemplary method of facilitating adjustment of one or more fitting parameters by an auditory prosthesis patient includes 1) receiving, by a fitting subsystem communicatively coupled to a sound processor, user input representative of a selection of a fitting parameter, 2) associating, by the fitting subsystem in response to the user input, the fitting parameter with a physical input mechanism that is a part of the sound processor, and 3) dynamically adjusting, by the fitting subsystem, a value of the fitting parameter in response to actuation by a user of the physical input mechanism.

Another exemplary method of facilitating adjustment of one or more fitting parameters by an auditory prosthesis patient includes 1) receiving, by a fitting subsystem communicatively coupled to a sound processor by way of a clinician's programming interface ("CPI") device, user input representative of a selection of a fitting parameter, 2) associating, by the fitting subsystem in response to the user input, the fitting parameter with a physical input mechanism that is a part of the CPI device, and 3) dynamically adjusting, by the fitting subsystem, a value of the fitting parameter in response to actuation by a user of the physical input mechanism.

An exemplary system for facilitating adjustment of one or more fitting parameters by an auditory prosthesis patient includes 1) a user interface facility configured to receive user input representative of a selection of a fitting parameter and 2) a fitting facility communicatively coupled to the user interface facility and configured to associate the fitting parameter with a physical input mechanism that is a part of a sound processor communicatively coupled to the system and dynamically adjust a value of the fitting parameter in response to actuation by a user of the physical input mechanism.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
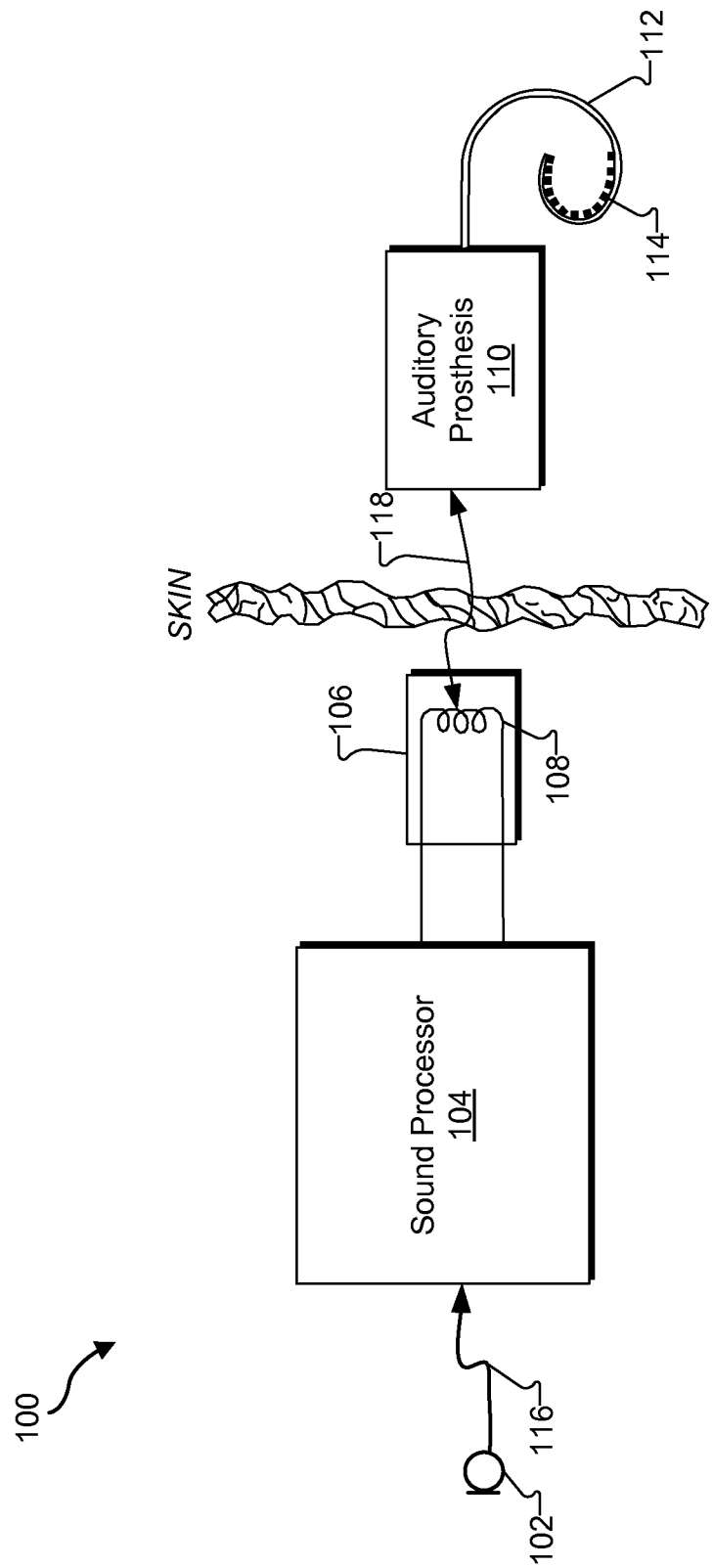
FIG. 1 illustrates an exemplary auditory prosthesis system according to principles described herein.

Methods and systems for facilitating adjustment of one or more fitting parameters by an auditory prosthesis patient are described herein. As described in more detail below, a fitting subsystem may be communicatively coupled to a sound processor and configured to receive user input representative of a selection of a fitting parameter. In response to the user input, the fitting subsystem may associate the fitting parameter with a physical input mechanism that is a part of the sound processor (or, in some examples, part of a clinician's programming interface device) and dynamically adjust a value of the fitting parameter in response to actuation by a user of the physical input mechanism.

To illustrate, an audiologist may utilize a fitting subsystem (e.g., a fitting station or computer) to adjust "most-comfortable level" (or "M level") associated with an auditory prosthesis system (e.g., a cochlear implant system) used by a patient. As used herein, an M level represents a stimulation level which, when applied to a given electrode associated with a particular channel, produces a sensed perception of sound by the patient that is moderately loud, or comfortably loud, but not so loud that the perceived sound is uncomfortable. Hence, determination of an optimal M level typically relies on subjective feedback by the patient.

To facilitate adjustment of the M level, the audiologist may first communicatively couple a sound processor that is a part of the auditory prosthesis system to the fitting subsystem. The audiologist may then direct the fitting subsystem to associate the M level with a volume control knob (or any other physical input mechanism) that is a part of the sound processor. Once the M level has been associated with the volume control knob, the audiologist may release control of the M level to the patient. The patient may then use the volume control knob to adjust the M level until an optimal M level is identified.

Hence, the methods and systems described herein allow the patient (as opposed to the audiologist only) to make adjustments to a particular fitting parameter. Because the patient does not have to verbalize how he or she perceives the adjustments, an optimal value for the fitting parameter may be determined more quickly than if the audiologist has to make the adjustments in response to patient feedback.

Moreover, the methods and systems described herein are advantageous in that they utilize hardware already present during a fitting session (i.e., a physical input mechanism that is a part of the sound processor or the clinician's programming interface device). This obviates the need for separate user input devices (e.g., joysticks, dials, etc.) to be coupled to the fitting subsystem. A physical input mechanism that is a part of the sound processor may also be easier for some types of patients to operate than peripheral devices (e.g., a keyboard and/or a mouse) associated with the fitting subsystem. For example, some older patients may not be familiar with and/or comfortable using a keyboard and/or mouse connected to a computer. However, these patients may more readily know how to operate a simple volume control knob.

To facilitate an understanding of the methods and systems described herein, an exemplary auditory prosthesis system 100 will be described in connection with FIG. 1. As shown in FIG. 1, auditory prosthesis system 100 may include a microphone 102, a sound processor 104, a headpiece 106 having a coil 108 disposed therein, an auditory prosthesis 110, and a lead 112 with a plurality of electrodes 114 disposed thereon. Additional or alternative components may be included within auditory prosthesis system 100 as may serve a particular implementation.

As shown in FIG. 1, microphone 102, sound processor 104, and headpiece 106 may be located external to an auditory prosthesis patient, and auditory prosthesis 110, lead 112, electrodes 114 may be implanted subcutaneously with the patient. In some alternative examples, microphone 102 and/or sound processor 104 may also be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct auditory prosthesis 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing program loaded on sound processor 104 to generate appropriate stimulation parameters for controlling auditory prosthesis 110. In certain examples, sound processor may 104 may include multiple sound processing programs loaded thereon such that a patient may select, from the multiple sound processing programs, which sound processing program to utilize to generate stimulation parameters. Accordingly, the patient may select a sound processing program that is well suited for a particular situation.

Sound processor 104 may include or be implemented by a behind-the-ear ("BTE") unit, an off-the-ear speech processor (i.e., a speech processor configured to be worn off the ear, such as a portable speech processor ("PSP")), and/or any other sound processing unit as may serve a particular implementation. Exemplary components of sound processor 104 will be described in more detail below.

Sound processor 104 may be configured to transcutaneously transmit one or more control parameters and/or one or more power signals to auditory prosthesis 110 with coil 108 by way of a communication link 118. These control parameters may be configured to specify one or more stimulation parameters, operating parameters, and/or any other parameter by which auditory prosthesis 110 is to operate as may serve a particular implementation. Exemplary control parameters include, but are not limited to, stimulation current levels, volume control parameters, program selection parameters, operational state parameters (e.g., parameters that turn a sound processor and/or an auditory prosthesis on or off), audio input source selection parameters, fitting parameters, noise reduction parameters, microphone sensitivity parameters, microphone direction parameters, pitch parameters, timbre parameters, sound quality parameters, most comfortable current levels ("M" levels), threshold current levels ("T" levels), clipping levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within auditory prosthesis 110. In this manner, control parameters and power signals may be wirelessly transmitted between sound processor 104 and auditory prosthesis 110 via communication link 118. It will be understood that data communication link 118 may include a bi-directional communication link and/or one or more dedicated uni-directional communication links. In some alternative embodiments, sound processor 104 and auditory prosthesis 110 may be directly connected with one or more wires or the like.

Auditory prosthesis 110 may include any type of implantable stimulator that may be used in association with the systems and methods described herein. For example, auditory prosthesis 110 may include an implantable cochlear stimulator. In some alternative implementations, auditory prosthesis 110 may include a brainstem implant and/or any other type of auditory prosthesis that may be implanted within a patient and configured to apply stimulation to one or more stimulation sites located along an auditory pathway of a patient.

In some examples, auditory prosthesis 110 may be configured to generate electrical stimulation representative of an audio signal detected by microphone 102 in accordance with one or more stimulation parameters transmitted thereto by sound processor 104. Auditory prosthesis 110 may be further configured to apply the electrical stimulation to one or more stimulation sites within the patient via one or more electrodes 114 disposed along lead 112. In some examples, auditory prosthesis 110 may include a plurality of independent current sources each associated with a channel defined by one or more of electrodes 114. In this manner, different stimulation current levels may be applied to multiple stimulation sites simultaneously by way of multiple electrodes 114. In such examples, auditory prosthesis system 100 may be referred to as a "multi-channel auditory prosthesis system."

To facilitate application of the electrical stimulation generated by auditory prosthesis 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
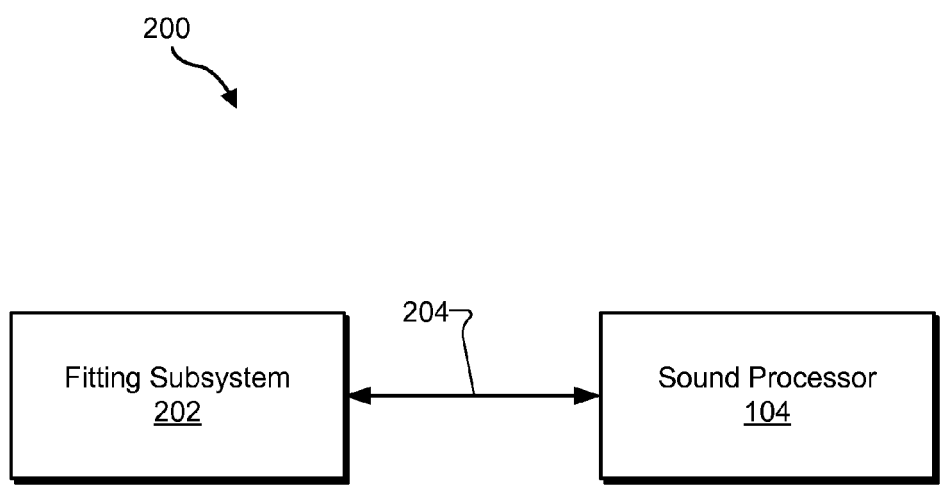
FIG. 2 illustrates an exemplary auditory prosthesis fitting system according to principles described herein.

FIG. 2 illustrates an exemplary auditory prosthesis fitting system 200 (or simply "fitting system 200") that may be used to fit auditory prosthesis system 100 to a patient. As used herein, the terms "fitting a sound processor to a patient" and "fitting an auditory prosthesis system to a patient" will be used interchangeably to refer to performing one or more fitting procedures associated with sound processor 104 and/or any other component of auditory prosthesis system 100. Such fitting procedures may include, but are not limited to, adjusting one or more fitting parameters, measuring one or more electrode impedances, performing one or more neural response detection operations, and/or performing one or more testing, diagnostic, and/or troubleshooting operations associated with the auditory prosthesis system.

As shown in FIG. 2, fitting system 200 may include a fitting subsystem 202 configured to be selectively and communicatively coupled to sound processor 104 of auditory prosthesis system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting procedures and/or operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

Figure 3:
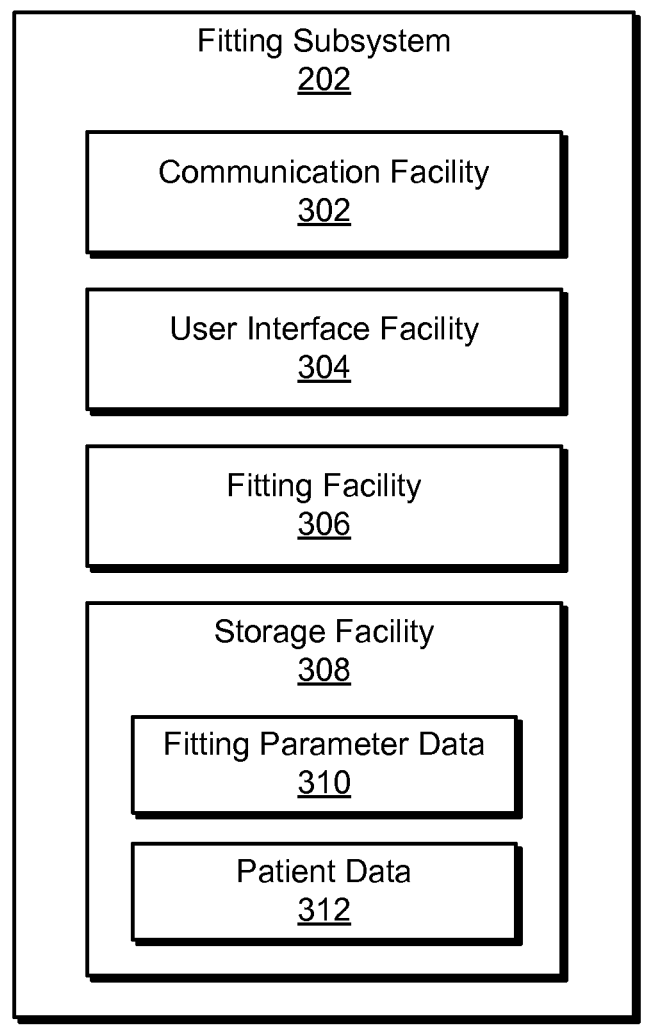
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, and a storage facility 308, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

In some examples (e.g., during a fitting of a bilateral auditory prosthesis patient), communication facility 302 may facilitate selective and/or concurrent communication between multiple sound processors (e.g., right and left sound processors). In this manner, communication facility 302 may be configured to communicate with a first auditory prosthesis associated with a first ear (e.g., the right ear) of the patient by way of a first sound processor and a second auditory prosthesis associated with a second ear (e.g., the left ear) of the patient by way of a second sound processor.

Communication facility 302 may additionally or alternatively be configured to facilitate communication between fitting subsystem 302 and one or more other devices. For example, communication facility 302 may be configured to facilitate communication between fitting subsystem 202 and one or more computing devices (e.g., by way of the Internet and/or one or more other types of networks).

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display.

In some examples, user interface facility 304 may be configured to receive (e.g., by way of one or more GUIs) user input representative of a selection of a fitting parameter that is to be adjusted during a fitting procedure. As used herein, a "fitting parameter" refers to any parameter that may be adjusted in order to fit an auditory prosthesis system to a patient. For example, exemplary fitting parameters include, but are not limited to, M levels, minimum threshold levels (or "T levels"), loudness levels, loudness balancing parameters, bilateral balancing parameters, and/or any other parameter that may be adjusted in accordance with patient feedback.

As mentioned above, an M level represents a stimulation level which, when applied to a given electrode associated with a particular channel, produces a sensed perception of sound by the patient that is moderately loud, or comfortably loud, but not so loud that the perceived sound is uncomfortable. A T level generally represents the minimum stimulation level which, when applied to a given electrode associated with a particular channel, produces a sensed perception of sound by the patient at least fifty percent of the time. A loudness level represents a volume or loudness of sound as perceived by an auditory prosthesis patient. A loudness balancing parameter refers to a parameter that may govern a relative loudness between channels or between signals presented to the left and right ears of a bilateral auditory prosthesis patient. Determining an optimal value for each of these fitting parameters may rely on patient feedback.

Fitting facility 306 may be configured to perform one or more of the fitting procedures and/or operations described herein. For example, fitting facility 306 may be configured to define and/or adjust one or more fitting parameters, direct sound processor 104 to measure one or more electrode impedances, perform one or more neural response detection operations, and/or perform one or more testing, diagnostic, and/or troubleshooting operations associated with auditory prosthesis system 100.

For example, fitting facility 306 may associate, in response to user input representative of a selection of a fitting parameter, the selected fitting parameter with a physical input mechanism (e.g., a volume control knob) that is a part of a sound processor (e.g., sound processor 104) communicatively coupled to fitting subsystem 202. Additionally or alternatively, fitting facility 306 may associate the selected fitting parameter with a physical input mechanism that is a part of a CPI device communicatively coupled to a sound processor.

Fitting facility 306 may associate a selected fitting parameter with a physical input mechanism (e.g., a volume control knob) that is a part of a sound processor or a CPI device in any suitable manner. For example, fitting facility 306 may utilize one or more software features to re-map a volume control knob from being associated with volume control to being associated with the selected fitting parameter. In this manner, as will be described below, rotation of the volume control knob by a user causes a corresponding adjustment of a value of the fitting parameter instead of a corresponding adjustment in volume.

Fitting facility 306 may be further configured to dynamically adjust a value of a fitting parameter in response to actuation by a user of a physical input mechanism within which the fitting parameter is associated. For example, in cases where the physical input mechanism comprises a volume control dial, fitting facility 306 may dynamically increase the value of the fitting parameter in response to a rotation of the volume control dial in a first direction (e.g., clockwise) and decrease the value of the fitting parameter in response to a rotation of the volume control dial in a second direction (e.g., counter-clockwise).

In some examples, fitting facility 306 may be configured to limit a range within which the value of a fitting parameter may be adjusted in response to user actuation of (or user interaction with) the physical input mechanism. For example, as will be described in more detail below, user interface facility 304 may receive additional user input specifying a limited adjustment range within which the value of a fitting parameter may be adjusted. In response, fitting facility 306 may set an adjustment range associated with the fitting parameter to be substantially equal to the limited adjustment range. The adjustment range may be set by fitting facility 306 in any suitable manner as may serve a particular implementation.

It will be recognized that the fitting facility 306 may associate any of a number of different fitting parameters with the physical input mechanism. For example, after being initially associated with a particular fitting parameter, the physical input mechanism may be re-associated with a different fitting parameter. To illustrate, the physical input mechanism may be initially associated with an M level. Subsequently, an audiologist may provide fitting subsystem 202 with additional user input specifying that a new fitting parameter (e.g., a T level) is to be associated with the physical input mechanism. In response, fitting facility 306 may disassociate the M level from the physical input mechanism and then associate the T level with the physical input mechanism.

In some examples, fitting facility 306 may be configured to set or adjust a sensitivity of the physical input mechanism. In other words, fitting facility 306 may specify an amount by which a value of a fitting parameter may be adjusted in response to an incremental actuation (e.g., incremental rotation) of the physical input mechanism. In this manner, an audiologist or other user may ensure that the value of a particular fitting parameter is not changed in a manner that causes discomfort or damage to the patient.

Fitting facility 306 may set or adjust a sensitivity of the physical input mechanism in any suitable manner. For example, user input facility 304 may receive user input (e.g., by way of one or more GUIs) specifying a desired sensitivity of the physical input mechanism. In response, fitting facility 306 may set the sensitivity of the physical input mechanism to be substantially equal to the desired sensitivity. Subsequently, fitting facility 306 may adjust the value of the fitting parameter in accordance with the desired sensitivity.

It will be recognized that even after an audiologist has turned over control of a particular fitting parameter to a patient, the audiologist may regain control of the fitting parameter at any time. For example, a patient may be in the middle of adjusting a value of a particular fitting parameter when the patient or audiologist decides that it would be better for the audiologist to continue adjusting the fitting parameter. The audiologist may then perform subsequent adjustments to the fitting parameter using a keyboard, mouse, or any other input device. In some examples, as soon as fitting facility 306 detects that the fitting parameter has been adjusted by something other than actuation of the physical input mechanism (i.e., that the audiologist has taken over control of the fitting parameter), fitting facility 306 may automatically prevent further adjustments to the fitting parameter by the physical input mechanism.

Storage facility 308 may be configured to maintain fitting parameter data 310 representative of or associated with one or more fitting parameters, patient data 312 representative of data descriptive of or otherwise associated with one or more auditory prosthesis patients, and/or any other type of data as may serve a particular implementation.

Figure 4:
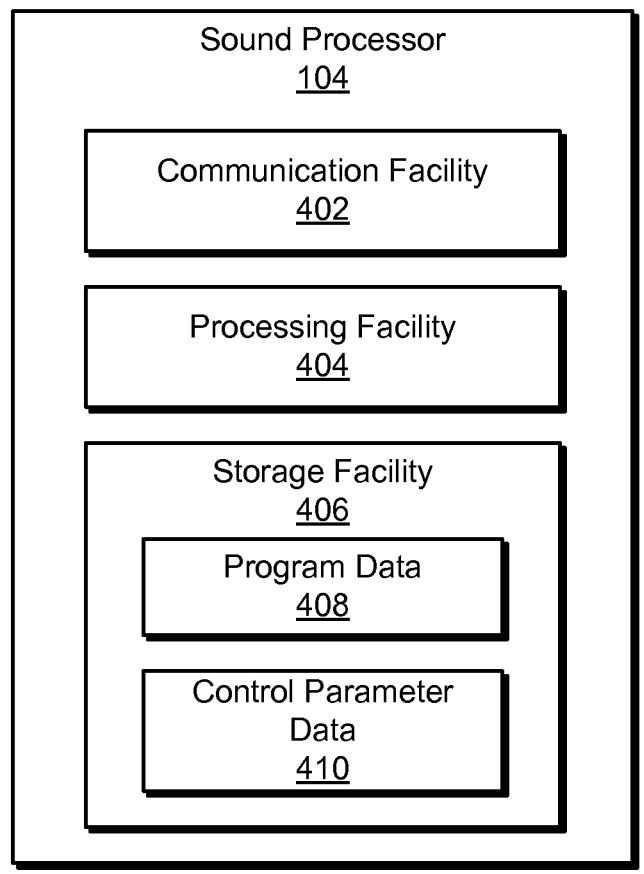
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and auditory prosthesis 110. For example, communication facility 402 may include transceiver components configured to wirelessly transmit data (e.g., control parameters and/or power signals) to auditory prosthesis 110 and/or wirelessly receive data from auditory prosthesis 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of auditory prosthesis 110 (e.g., one or more stimulation parameters defining the electrical stimulation to be generated and applied by auditory prosthesis 110). Processing facility 404 may be configured to operate in accordance with one or more sound processing programs and/or control parameters loaded onto sound processor 104 by fitting subsystem 202 and/or otherwise stored within storage facility 406.

Storage facility 406 may be configured to maintain program data 408 representative of one or more sound processing programs loaded onto sound processor 104 and control parameter data 410 representative of one or more control parameters. Storage facility 406 may be configured to maintain additional or alternative data as may serve a particular implementation.

Figure 5:
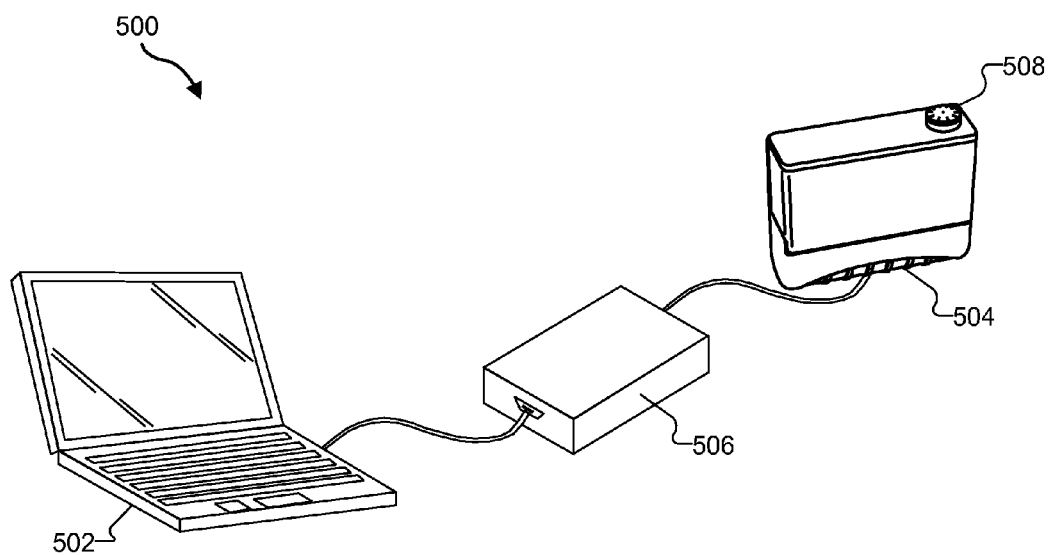
FIG. 5 illustrates an exemplary implementation of the auditory prosthesis fitting system of FIG. 2 according to principles described herein.

FIG. 5 illustrates an exemplary implementation 500 of fitting system 200. In implementation 500, a fitting station 502 may be selectively and communicatively coupled to an off-the-ear sound processor 504 (or simply "sound processor 504") by way of a CPI device 506.

Fitting station 502 may include any suitable computing device and/or combination of computing devices and be configured to perform one or more of the fitting operations described herein. Fitting station 502 may be utilized by an audiologist, a clinician, and/or any other user to fit sound processor 504 to a patient.

As shown, sound processor 504 is configured to be worn by a patient off the ear. In other words, sound processor 504 may be worn or carried by a patient at any location other than behind or on the ear. For example, sound processor module 102 may be secured to a piece of clothing worn by the patient, carried in a pocket or pouch, and/or otherwise carried by the patient. It will be recognized that sound processor 504 may alternatively include a sound processor configured to be worn behind or on the ear or any other type of sound processor as may serve a particular implementation.

As illustrated in FIG. 5, sound processor 504 may include a volume control knob 508. It will be recognized sound processor 504 may additionally or alternatively include any other type of physical input mechanism. For example, sound processor 504 may additionally or alternatively include a sensitivity control knob, one or more levers, buttons, etc. configured to serve as a physical input mechanism.

CPI device 506 may be configured to facilitate communication between fitting station 502 and sound processor 504. In some examples, CPI device 506 may be selectively and communicatively coupled to fitting station 502 and/or sound processor 504 by way of one or more ports included within fitting station 502 and sound processor 504.

It will be recognized that fitting station 502 may be concurrently coupled to more than one sound processor 504. For example, fitting station 502 may be coupled to two sound processors 504 (e.g., by way of two CPI devices 506) when a bilateral auditory prosthesis patient is being fitted.

Figure 6:
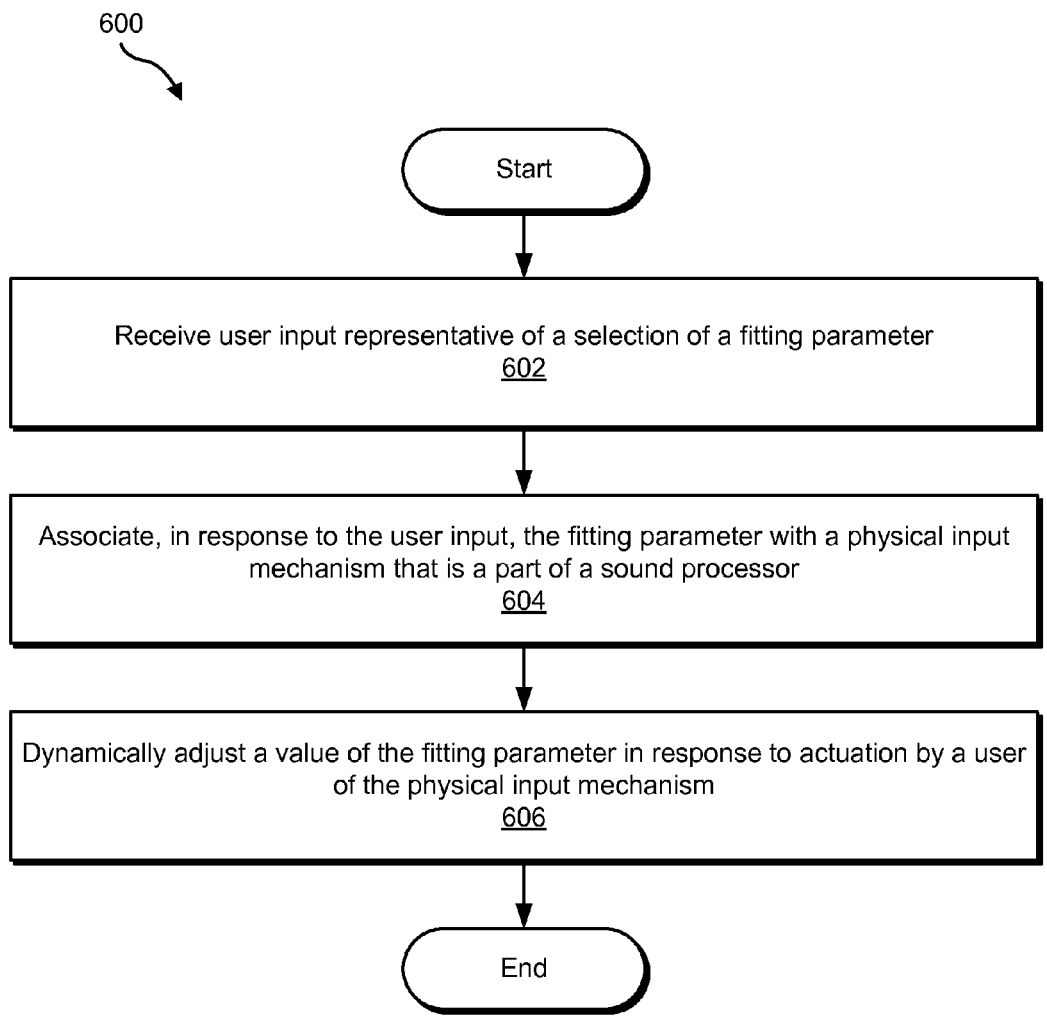
FIG. 6 illustrates an exemplary method of facilitating adjustment of one or more fitting parameters by an auditory prosthesis patient according to principles described herein.

FIG. 6 illustrates an exemplary method 600 of facilitating adjustment of one or more fitting parameters by an auditory prosthesis patient. While FIG. 6 illustrates exemplary steps according to one embodiment, other embodiments may omit, add to, reorder, combine, and/or modify any of the steps shown in FIG. 6. One or more of the steps shown in FIG. 6 may be performed by any component or combination of components of fitting subsystem 202 and/or fitting station 502.

In step 602, a fitting subsystem communicatively coupled to a sound processor receives user input representative of a selection of a fitting parameter. Step 602 may be performed in any of the ways described herein.

In step 604, in response to the user input, the fitting subsystem associates the fitting parameter with a physical input mechanism that is a part of the sound processor. Step 604 may be performed in any of the ways described herein.

In step 606, the fitting subsystem dynamically adjusts a value of the fitting parameter in response to actuation by a user of the physical input mechanism. Step 606 may be performed in any of the ways described herein.

Various implementations of method 600 will now be described. It will be recognized that the implementations described herein are merely illustrative of the many different implementations that may be realized in accordance with method 600.

Figure 7:
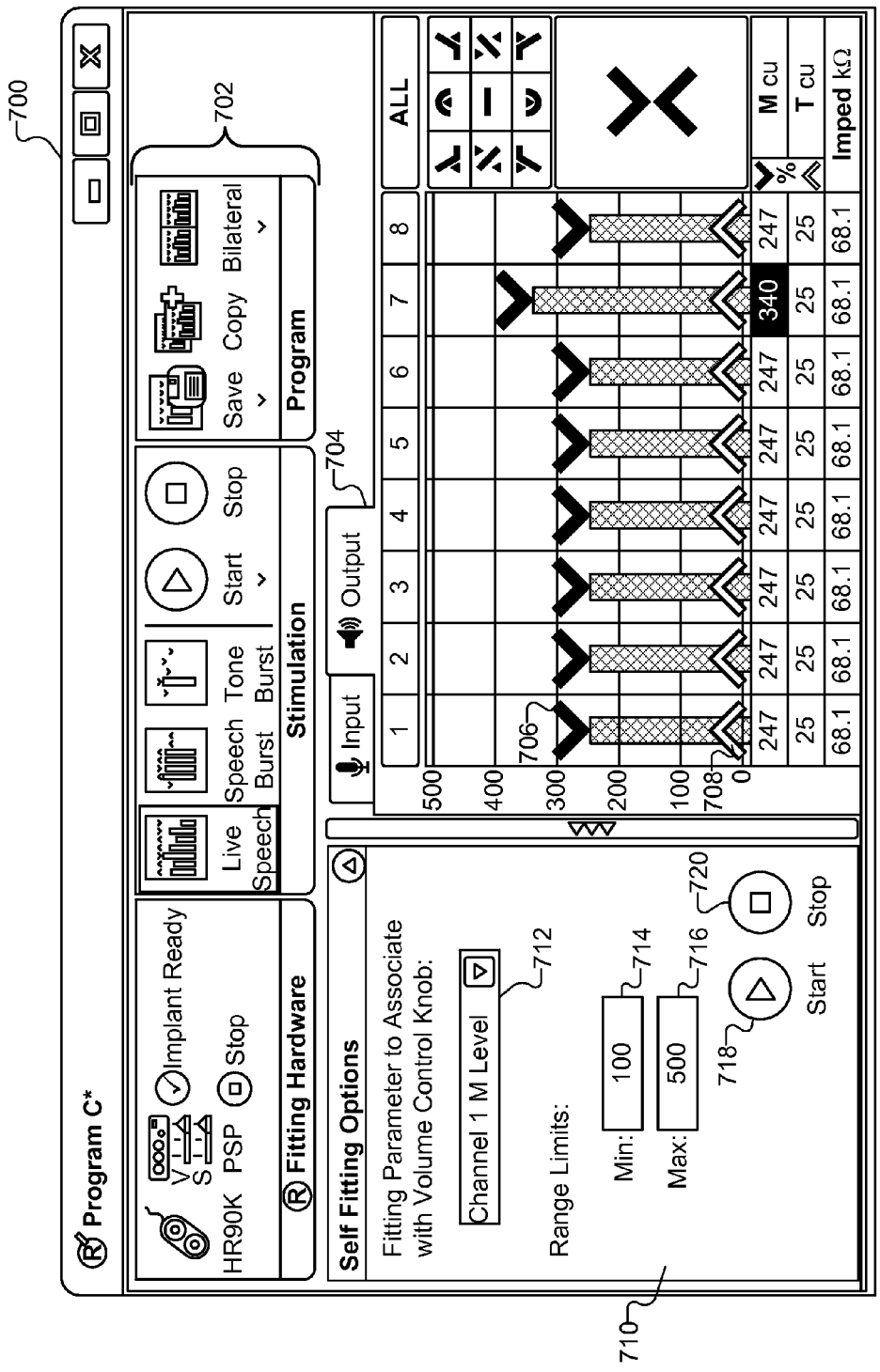
FIG. 7 shows an exemplary graphical user interface ("GUI") that may be configured to facilitate association of a fitting parameter with a physical input mechanism that is a part of a sound processor according to principles described herein.

FIG. 7 shows an exemplary GUI 700 that may be presented by fitting subsystem 202 and that may be configured to facilitate association of a fitting parameter with a physical input mechanism that is a part of a sound processor. As shown, GUI 700 includes a variety of fitting options 702 available to an audiologist as well as a graphical representation 704 of various fitting parameters associated with a particular patient and that may be adjusted in accordance with input provided by the audiologist and/or patient. For example, various markers (e.g., markers 706 and 708) may be displayed within GUI 700 and configured to graphically represent an M level and a T level of various channels associated with an auditory prosthesis system. It will be recognized that other types of fitting parameters may be graphically represented within GUI 700 or within any other GUI displayed by fitting subsystem 202.

To associate a particular fitting parameter with a physical input mechanism that is a part of a sound processor and/or CPI device, the audiologist may select one or more "self fitting" options 710 displayed within GUI 700. For example, the audiologist may associate one or more of the M levels and/or T levels represented by the markers displayed within GUI 700 with a volume control knob of the sound processor by selecting the desired fitting parameter(s) from a drop-down menu 712. In the example of FIG. 7, GUI 700 shows that an M level corresponding to a particular channel (i.e., channel 1) has been selected to be associated with the volume control knob. The audiologist may also specify a particular adjustment range for the selected fitting parameter by inputting a minimum value in field 714 and a maximum value in field 716. In this manner, the patient may only adjust the M level for channel 1 to a value that is included in a range defined by the minimum and maximum values.

When the audiologist is ready to hand over control of the fitting parameter to the patient, he or she may select a "start" option 718. At this point, the patient may rotate the volume control knob to adjust the M level associated with channel 1. As the patient makes adjustments to the M level, fitting subsystem 202 directs auditory prosthesis 110 to stimulate channel 1 with a corresponding stimulation current level. In this manner, the patient may perceive an effect of the adjustment. In some examples, the position of marker 706 may be adjusted in real-time to graphically represent the adjustment to the channel 1 M level.

Subsequently, when the audiologist desires to take back control of the fitting parameter, he or she may select a "stop" option 720. A different fitting parameter (e.g. the T level associated with marker 708) may then be associated with the volume control knob in a similar manner so that the patient may adjust the T level to a desired value.

It will be recognized that the example provided in connection with FIG. 7 is merely illustrative of the many different examples of allowing a patient to adjust a fitting parameter that may be realized in connection with the methods and systems described herein. For example, fitting subsystem 202 may present another GUI configured to facilitate adjustment by a patient of a loudness balancing parameter. To illustrate, fitting subsystem 202 may present a first tone to the right ear of a bilateral auditory prosthesis patient and a second tone to the left ear of the patient. The patient may then adjust a relative loudness level of the tones by actuating a physical input mechanism that is a part of the sound processor until the patient perceives that the loudness levels are balanced.

Figure 8:
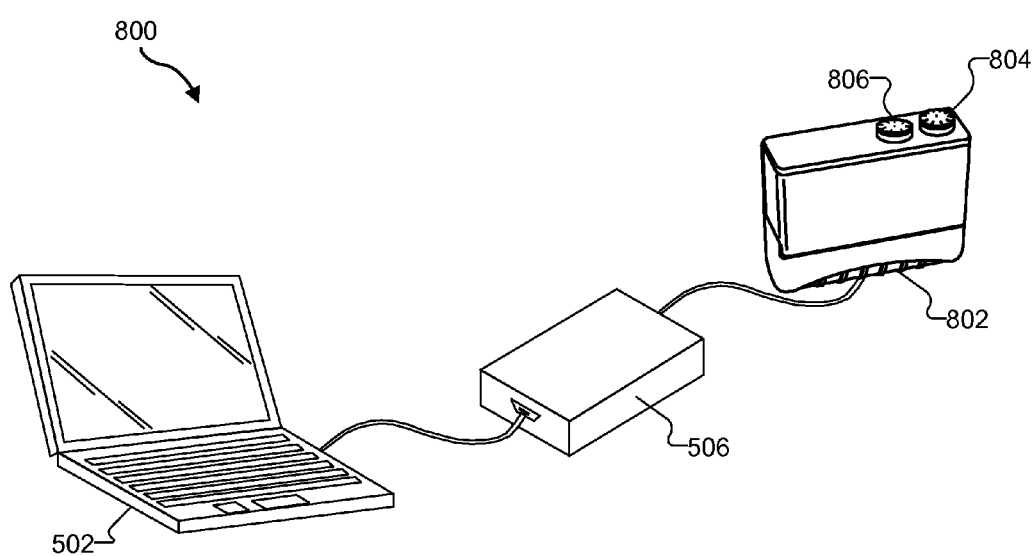
FIG. 8 illustrates an exemplary configuration in which a sound processor includes two physical input mechanisms according to principles described herein.

In some examples, a sound processor may include multiple physical input mechanisms. For example, FIG. 8 illustrates an exemplary configuration 800 in which a sound processor 802 includes two physical input mechanisms. In particular, sound processor 802 includes a volume control knob 804 and a sensitivity control knob 806. In this example, fitting subsystem 202 may associate a first fitting parameter with volume control knob 804 and a second fitting parameter with sensitivity control knob 806. In this manner, the patient may concurrently adjust two fitting parameters by adjusting both knobs 804 and 806.

Figure 9:
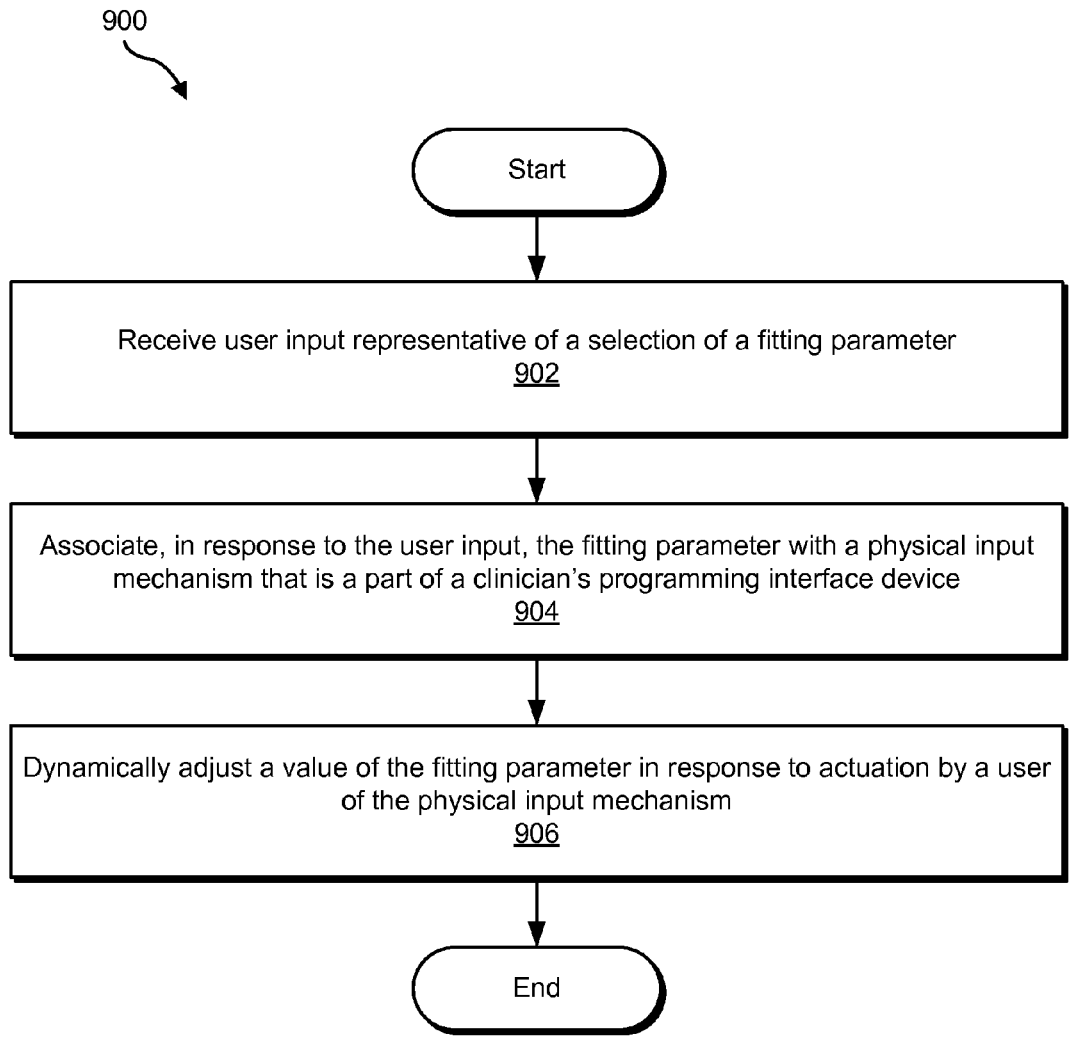
FIG. 9 illustrates another exemplary method of facilitating adjustment of one or more fitting parameters by an auditory prosthesis patient according to principles described herein.

FIG. 9 illustrates another exemplary method 900 of facilitating adjustment of one or more fitting parameters by an auditory prosthesis patient. While FIG. 9 illustrates exemplary steps according to one embodiment, other embodiments may omit, add to, reorder, combine, and/or modify any of the steps shown in FIG. 9. One or more of the steps shown in FIG. 9 may be performed by any component or combination of components of fitting subsystem 202 and/or fitting station 502.

In step 902, a fitting subsystem communicatively coupled to a sound processor by way of a clinician's programming interface device receives user input representative of a selection of a fitting parameter. Step 902 may be performed in any of the ways described herein.

In step 904, in response to the user input, the fitting subsystem associates the fitting parameter with a physical input mechanism that is a part of the clinician's programming interface device. Step 904 may be performed in any of the ways described herein.

In step 906, the fitting subsystem dynamically adjusts a value of the fitting parameter in response to actuation by a user of the physical input mechanism. Step 906 may be performed in any of the ways described herein.

Figure 10:
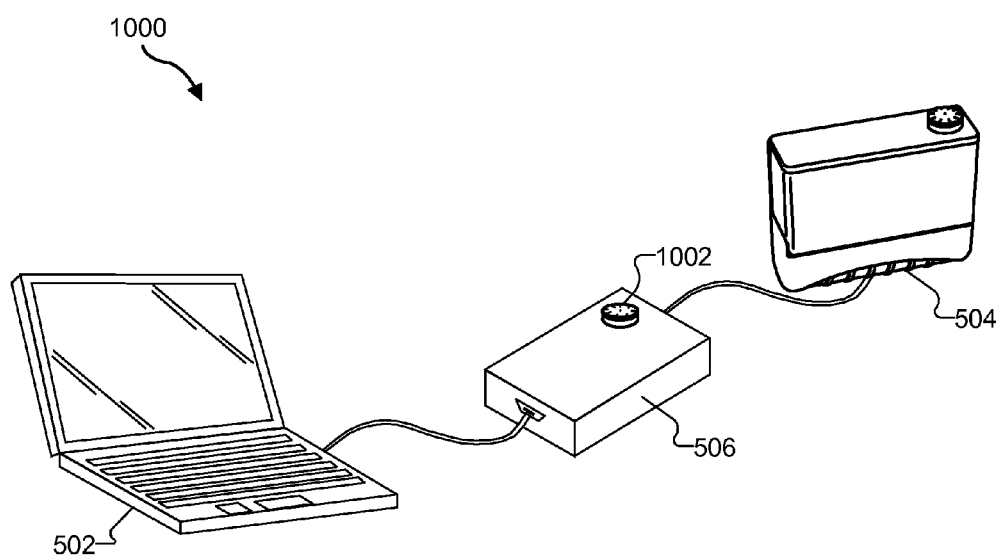
FIG. 10 illustrates an exemplary implementation of the auditory prosthesis fitting system of FIG. 2 according to principles described herein.

FIG. 10 shows an exemplary configuration 1000 of fitting system 200 that implements method 900. As shown, CPI device 506 includes a physical input mechanism 1002, which may include any of the physical input mechanisms described herein. Fitting station 502 may associate a fitting parameter with physical input mechanism 1002 in any of the ways described herein in order to facilitate a user adjusting the fitting parameter by interacting with physical input mechanism 1002.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 11:
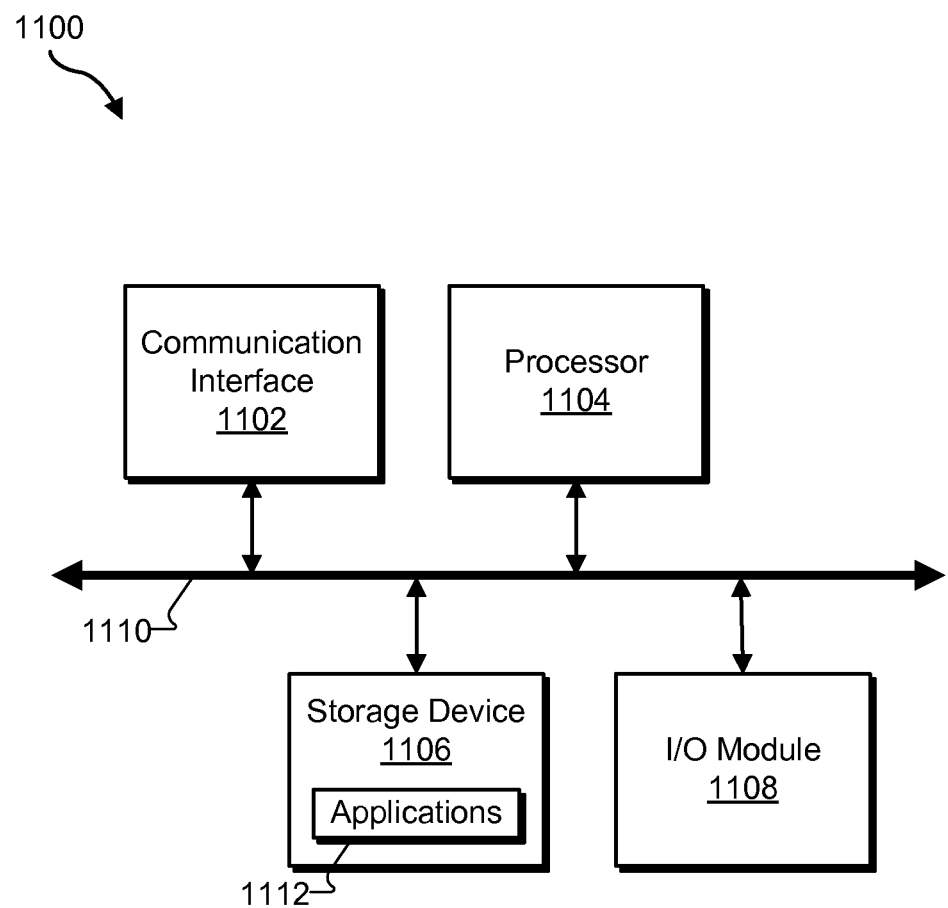
FIG. 11 illustrates an exemplary computing device according to principles described herein.

FIG. 11 illustrates an exemplary computing device 1100 that may be configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, and any other suitable interface. Communication interface 1102 may additionally or alternatively provide such a connection through, for example, a local area network (such as an Ethernet network), a personal area network, a telephone or cable network, a satellite data connection, a dedicated URL, or any other suitable connection. Communication interface 1102 may be configured to interface with any suitable communication media, protocols, and formats, including any of those mentioned above.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another non-transitory computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1106. For example, data representative of one or more executable applications 1112 (which may include, but are not limited to, one or more of the software applications described herein) configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1100. For example, one or more applications 1112 residing within storage device 1106 may be configured to direct processor 1104 to perform one or more processes or functions associated with communication facility 302, user interface facility 304, fitting facility 306, communication facility 402, and/or processing facility 404. Likewise, storage facility 308 and/or storage facility 406 may be implemented by or within storage device 1106.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow.

For example, certain features of one embodiment described herein may be combined with or substituted for features of another embodiment described herein. The description and drawings are accordingly to be regarded in an illustrative rather than a restrictive sense.

What is claimed is:

1. A method comprising:
providing, by a fitting subsystem separate from and communicatively coupled to a sound processor that is communicatively coupled to an auditory prosthesis implanted within a patient, a graphical user interface to facilitate user interaction with the fitting subsystem during a fitting session during which the fitting subsystem fits the sound processor to the patient;
receiving, by the fitting subsystem by way of the graphical user interface during the fitting session, user input representative of a selection of a fitting parameter;
associating, by the fitting subsystem in response to the user input received by way of the graphical user interface during the fitting session, the fitting parameter with a physical input mechanism that is a part of the sound processor; and
dynamically adjusting, by the fitting subsystem during the fitting session, a value of the fitting parameter in response to actuation by a user of the physical input mechanism.

2. The method of claim 1, further comprising:
receiving, by the fitting subsystem, additional user input representative of a selection of an additional fitting parameter;
disassociating, by the fitting subsystem in response to the additional user input, the fitting parameter from the physical input mechanism; and
associating, by the fitting subsystem in response to the additional user input, the additional fitting parameter with the physical input mechanism.

3. The method of claim 2, further comprising:
dynamically adjusting, by the fitting subsystem, a value of the additional fitting parameter in response to additional actuation by the user of the physical input mechanism.

4. The method of claim 1, further comprising:
receiving, by the fitting subsystem, additional user input specifying a limited adjustment range within which the value of the fitting parameter can be adjusted; and
setting, by the fitting subsystem in response to the additional user input, an adjustment range associated with the fitting parameter to be substantially equal to the limited adjustment range.

5. The method of claim 1, further comprising:
receiving, by the fitting subsystem, additional user input specifying a sensitivity of the physical input mechanism; and
performing, by the fitting subsystem, the dynamically adjusting in accordance with the specified sensitivity.

6. The method of claim 1, further comprising:
detecting, by the fitting subsystem, an adjustment to the value of the fitting parameter by an additional user; and
automatically preventing, by the fitting subsystem in response to the detecting, the user from performing one or more additional adjustments to the value of the fitting parameter.

7. The method of claim 1, further comprising:
receiving, by the fitting subsystem communicatively, additional user input representative of a selection of an additional fitting parameter;

associating, by the fitting subsystem in response to the user input, the additional fitting parameter with an additional physical input mechanism that is a part of the sound processor; and dynamically adjusting, by the fitting subsystem, a value of the additional fitting parameter in response to actuation by a user of the additional physical input mechanism.

8. The method of claim 1, wherein the user is the patient.

9. The method of claim 1, wherein the fitting parameter comprises a most comfortable loudness level, a minimum threshold level, a loudness level, or a loudness balancing parameter.

10. The method of claim 1, wherein the physical input mechanism comprises a volume control knob.

11. The method of claim 1, embodied as computer-executable instructions on at least one non-transitory computer-readable medium.

12. A method comprising:

providing, by a fitting subsystem separate from and communicatively coupled by way of a clinician's programming interface ("CPI") device to a sound processor that is communicatively coupled to an auditory prosthesis implanted within a patient, a graphical user interface to facilitate user interaction with the fitting subsystem during a fitting session during which the fitting subsystem fits the sound processor to the patient;

receiving, by the fitting subsystem by way of the graphical user interface during the fitting session, user input representative of a selection of a fitting parameter associated with the sound processor;

associating, by the fitting subsystem in response to the user input received by way of the graphical user interface during the fitting session, the fitting parameter with a physical input mechanism that is a part of the CPI device; and dynamically adjusting, by the fitting subsystem during the fitting session, a value of the fitting parameter associated with the sound processor in response to actuation by a user of the physical input mechanism that is a part of the CPI device.

13. The method of claim 12, further comprising:

receiving, by the fitting subsystem, additional user input representative of a selection of an additional fitting parameter;

disassociating, by the fitting subsystem in response to the additional user input, the fitting parameter from the physical input mechanism; and associating, by the fitting subsystem in response to the additional user input, the additional fitting parameter with the physical input mechanism.

14. The method of claim 13, further comprising:

dynamically adjusting, by the fitting subsystem, a value of the additional fitting parameter in response to additional actuation by the user of the physical input mechanism.

15. The method of claim 12, further comprising:

receiving, by the fitting subsystem, additional user input specifying a limited adjustment range within which the value of the fitting parameter can be adjusted; and setting, by the fitting subsystem in response to the additional user input, an adjustment range associated with the fitting parameter to be substantially equal to the limited adjustment range.

16. The method of claim 12, further comprising:

receiving, by the fitting subsystem, additional user input specifying a sensitivity of the physical input mechanism; and performing, by the fitting subsystem, the dynamically adjusting in accordance with the specified sensitivity.

17. The method of claim 12, further comprising:

receiving, by the fitting subsystem communicatively, additional user input representative of a selection of an additional fitting parameter;

associating, by the fitting subsystem in response to the user input, the additional fitting parameter with an additional physical input mechanism that is a part of the sound processor; and dynamically adjusting, by the fitting subsystem, a value of the additional fitting parameter in response to actuation by a user of the additional physical input mechanism.

18. The method of claim 12, embodied as computer-executable instructions on at least one non-transitory computer-readable medium.

19. A system separate from and communicatively coupled to a sound processor that is communicatively coupled to an auditory prosthesis implanted within a patient, the system comprising:

a user interface facility that provides a graphical user interface to facilitate user interaction with the system during a fitting session during which the system fits the sound processor to the patient, and receives, by way of the graphical user interface during the fitting session, user input representative of a selection of a fitting parameter; and a fitting facility communicatively coupled to the user interface facility and that associates, in response to the user input received by way of the graphical user interface during the fitting session, the fitting parameter with a physical input mechanism that is a part of the sound processor, and dynamically adjusts a value of the fitting parameter in response to actuation by a user of the physical input mechanism.

* * * * *